US005728437A

United States Patent [19]
Nygren et al.

[11] Patent Number: 5,728,437
[45] Date of Patent: Mar. 17, 1998

[54] ARTICLES EXHIBITING A BLOOD-COMPATIBLE SURFACE LAYER AND PROCESS FOR PROVIDING ARTICLES WITH SUCH A SURFACE LAYER

[75] Inventors: Håkan Bo Nygren, Billdal; Emanuel Johan Stenberg, Göteborg, both of Sweden

[73] Assignee: Astra Meditec Aktiebolag, Molndal, Sweden

[21] Appl. No.: 346,338

[22] Filed: Nov. 29, 1994

Related U.S. Application Data

[63] Continuation of Ser. No. 974,321, Nov. 10, 1992, abandoned, which is a continuation of Ser. No. 465,118, Feb. 13, 1990, abandoned.

[30] Foreign Application Priority Data

Aug. 26, 1987 [SE] Sweden ................................ 8703310

[51] Int. Cl.$^6$ .................................................. B29D 22/00
[52] U.S. Cl. ................. 428/35.7; 428/35.6; 428/36.9; 428/36.91; 604/265; 604/266
[58] Field of Search .......................... 428/35.7, 35.6, 428/36.9, 36.91; 604/265, 266

[56] References Cited

U.S. PATENT DOCUMENTS

| | | | |
|---|---|---|---|
| 3,926,951 | 12/1975 | Lindenfors et al. | 260/231 |
| 4,008,047 | 2/1977 | Petersen | 422/48 |
| 4,279,795 | 7/1981 | Yamashita | 604/892 |
| 4,530,974 | 7/1985 | Munro | 525/329.4 |
| 4,543,282 | 9/1985 | Hamner et al. | 428/34.8 |
| 4,553,973 | 11/1985 | Edgren | 604/892 |
| 4,708,951 | 11/1987 | Inagaki | 514/57 |
| 4,876,126 | 10/1989 | Takemura et al. | 428/35.7 |

FOREIGN PATENT DOCUMENTS

| | | | |
|---|---|---|---|
| 1208557 | 7/1986 | Canada | 167/156 |
| 0166998 | 4/1984 | European Pat. Off. | |

OTHER PUBLICATIONS

Chemical Abstracts, vol. 102 (1985), abstract No. 67 368, Kenkya Hokoku–Seni.
Kobunshi Zairoy Kenkyusho, 1982, (131), 11–22 (Jap).
Journal of Bioengeneering, vol. 2, p. 241–249, 1978, J.M. Courtney et al, "Polymer Modification nd Blood Compatibility".

*Primary Examiner*—James J. Seidleck
*Assistant Examiner*—Michael A. Williamson
*Attorney, Agent, or Firm*—White & Case

[57] ABSTRACT

Article exhibiting at least one surface of glass, metal or hydrophobic polymer coated with blood-compatible surface layer, in which the biocompatible surface layer consists of an adsorbed hydrophobized water-soluble polymer. Process for providing said articles by adsorption of hydrophobized water-soluble polymer. Use of such a substrate material coated with said surface layer for manufacture of medical articles having a blood-compatible surface.

8 Claims, No Drawings

ARTICLES EXHIBITING A BLOOD-COMPATIBLE SURFACE LAYER AND PROCESS FOR PROVIDING ARTICLES WITH SUCH A SURFACE LAYER

This application is a continuation of application Ser. No. 07/974,321, filed Nov. 10, 1992, abandoned, which is a continuation of application Ser. No. 07/465,118, filed Feb. 13, 1990 (abandoned).

FIELD OF THE INVENTION

The present invention relates to articles exhibiting a blood-compatible surface layer and methods for providing such articles with such a surface layer and in particular for providing articles useful within medicine. More particularly, the invention relates to articles exhibiting at least one surface of glass, metal or a hydrophobic polymer coated with a blood-compatible surface layer and processes for providing articles exhibiting at least one surface of glass, metal or a hydrophobic polymer with a coating of a blood-compatible surface layer, as well as the use of substrate material of glass, metal or hydrophobic polymer, coated with the surface layer of an adsorbed hydrophobized water-soluble polymer preferably a non-protein for manufacture of a medical article having a blood-compatible surface.

BACKGROUND OF THE INVENTION

Prior art technique to provide articles useful in medicine with a blood-compatible surface layer often comprises an alteration in the surface energy of the material. An improvement in the properties of various materials has been obtained by modifying the surface layers either to a more hydrophobic character or to a more hydrophilic character. Hydrophobization of the surface layer, for instance by the methylization of a glass surface, results in a decrease in the effectiveness of the surface activated coagulation system of the blood. However, proteins such as fibrinogen are bound comparatively firmly to such surface and to this protein layer certain cells, the thrombocytes, can be bound and activated whereafter coagulation is started even though it proceeds slowly. Hydrophilic surfaces, e.g. hydrolysed nylon or oxidized aluminium, have presented reduced binding of cells but the surface activated coagulation system is not prevented at these surfaces. The use of these surfaces in contact with blood thus implies the addition of anti-coagulants, for instance heparin to the blood.

Another prior art surface treatment technique for preventing coagulation comprises binding of anticoagulants into the surface layer. Heparin has primarily been used with this technique. Heparin is a hexoseamine-hexuronic acid polysaccharide which is sulphatized and has acid properties, i.e. heparin is an organic acid. According to DE-A-21 54 542 articles of an organic thermoplastic resin is first impregnated with an amino-silane coupling agent and the article thus treated is then reacted with an acid solution of heparin salt to the binding of heparin in the surface layer by means of ionic bonds. Surfaces thus treated with heparin have proved to reduce the coagulation reaction. A considerable disadvantage of these surfaces, however, is that the heparin treatment does not prevent the adherence of thrombocytes, which is a great problem in, for instance, heart-lung machines.

On the 10th Annual Meeting of the Society for Biomaterials (Washington D.C. Apr. 27, 1984) was described that polyethylenglycol surfaces on quartz minimize protein adsorption. Procedures for covalent binding of polyethylenglycol to surfaces have previously been described, e.g. in W086/02087. Polyion complexes formed between a cationic and an anionic cellulose derivative have also been found to have good blood-compatibilities (Ito, H. et.al., J. Appl. Polym. Sci., Vol. 32 (1986) 3413). Methods of covalent binding of water-soluble polymers to surfaces have also been described, e.g. in EP 166 998.

It is known that water-binding gels, for instance polyhydroxyalkylmethacrylate, reduce the adsorption of proteins and present a low adhesiveness to cells (Hoffman et al., Ann. N.Y. Acad. Sci., Vol. 283 (1977) 372). These properties are considered to be due to the fact that gels containing water give a low surface energy in the interface to the blood. The prior art technique for manufacturing of water-binding gels, however, is impaired by disadvantages such as complicated preparation technique and incomplete polymerization, which results in leakage of toxic monomers. A gel-like mixture of saccharose and glucose included in a matrix of the polysaccharide dextran or dextrin is used in accordance with previously known technique as a robe for the connection of blood-vessels. This mixture should have the effect that no toxicity to the patient occurs that the implantate is dissolved in the blood after some time. It is known that the neutral polysaccharide dextran is miscible with blood without provoking any coagulation reaction. Dextran has been used as a surface coating on glass, aluminium and silicon rubber, and has been shown to reduce blood coagulation during blood contact with these surfaces as described in W083/03977.

The adhesion of blood components to surfaces in contact with blood could be decreased by preadsorption of albumin to hydrophobic surfaces (Mosher, D. F, in: Interaction of blood with natural and artificial surfaces, Ed. Salzman, E. W., Dekker Inc 1981). The adsorbed albumin does not form a stable coating, but is desorbed during contact with blood and coagulation is induced although at a lower rate.

DISCLOSURE OF THE INVENTION

The object of the present invention is to provide articles useful within medicine with a blood-compatible surface layer. This means, for articles intended for use in contact with blood, that the article which is alien to the blood is treated in such a way that it does not induce coagulation or formation of thromboses.

The present invention affords technique for the surface treatment of material important for medical technology, such as glass, metal and hydrophobic polymers (e.g. polytetrafluoroethylene (PTFE)).

The article according to the invention which exhibits at least one surface of glass, metal or hydrophobic polymer coated with a blood-compatible surface layer, is characterized in that the blood-compatible surface layer consists of an adsorbed hydrophobized water-soluble polymer.

The process according to the invention for providing articles exhibiting at least one surface of glass, metal or hydrophobic polymer coated with blood-compatible surface layer, is characterized in that said substrate surface of the article, after hydrophobization when required, is exposed to a hydrophobized water-soluble polymer, which adsorbs to said substrate surface.

The substrate surface has to be hydrophobic before coating. For metals or metal oxides this can be achieved by methylization with silanes.

The polymers used in the present invention are hydrophobized derivatives of water-soluble polymers. This means that the polymers used are limited soluble in water depending on the degree of hydrophobization. Examples of possible polymers that could be hydrophobized and used as surface coating polymers are mentioned Natural water-soluble polymers
1) Starches, especially derivatives such as ethers
2) Celluloses, especially cellulose ethers
3) Other polysaccharides alginic acid, gum arabic, gum guar, gum tragacanth, tannin, tamarind and lignin Synthetic water-soluble polymers
1) PVA polyvinyl alcohol
2) Polyethylene oxides polyethylene oxide, polyethylene glycol
3) Acrylates sodium polyacrylate
4) Maleic anhydride polymers methyl vinyl ether-maleic anhydride copolymers
5) Phthalates polyhydroxy ethyl phthalates
6) Water-soluble polyesters polydimethylol propionate
7) Ketone aldehyde resins methyl isopropyl ketone formaldehyde resin
8) Acrylamides polyacrylamide
9) Polyvinyl pyrrolidone PVP
10) water-soluble nylon The water-soluble polymer used in this invention is a hydrophobized derivative of one of these polymers and it is characterized by the property of the ability to adsorb at hydrophobic surfaces. The hydrophobization of the polymer can be performed by binding of hydrocarbons to the polymer backbone. Examples of such hydrocarbons are alkyl-groups, benzyl-groups or alkenyl-groups. The hydrophobization renders the polymer partly insoluble in water with a flocculation above a certain temperature or above a certain ionic strength.

The substrate surface is exposed to a solution of the polymer at a temperature below flocculation and at a salt concentration below flocculation. The hydrophobized polymers adsorb strongly to hydrophobic surfaces. Preferred polymers should have a flocculation temperature of about 35°–40° C.

For example, the hydrophobic surface of glass, metal or a polymer, e.g., polytetrafluoroethylene, may be exposed to a solution of an alkylated cellulose, such as ethyl hydroxyl cellulose having a flocculation temperature of about 35°–40° C., at a temperature below the flocculation temperature so as to provide the article of the invention.

The treated surface proves biologically inert and surfaces treated in this way give reduced adsorption of proteins, adherence of cells and coagulation. The adsorbed polymer is not exchanged by plasma proteins.

The process according to the present invention can be applied within many fields. Thus, in heart-lung machines there are used many details which are made of aluminum which can easily be treated by methyl-silane to get a hydrophobic surface.

The process according to the present invention is ideally suited for treatment of venous catheters. These are often manufactured in PTFE and this material is normally not blood compatible. For this material it is also difficult to find appropriate processes for covalent coupling of: hydrophilic polymers.

The invention may also be applied in other connections, for instance, for treatment of articles of hydrophobic plastics for sampling and/or storage of blood.

The invention will in the following be illustrated by a working example but is not limited thereto and hence modifications are of course conceivable within the limits of the claims.

WORKING EXAMPLE

Coating procedure a) The polymer is purified and isolated by repeated heat flocculation and centrifugation.

b) A polytetrafluoroethylene tube (teflon), diameter 3 mm, and a polyurethane-robe, diameter 3 nun, were immersed in a solution of ethyl-hydroxyethyl-cellulose (EHEC, 1 g/l, prepared according to US 3,926,951 ) in distilled water for 20 hours in room temperature. The tubes were rinsed in saline for 1 minute.

Experimental tests

Two different tests were performed. Incubation with a solution of fibrinogen at high concentration was performed in order to detect exchange reactions between the polymer and plasma protein. Incubation with whole blood followed by measurement of released thromboglobulin was used to measure the stability of the polymer coating and the activation of platelets at the surface.

Fibrinogen adsorption a) Coated and non-coated tubes were incubated in a solution of human fibrinogen (1 g/l) in saline for 30 minutes at room temperature.

b) The tubes were rinsed in saline for 10 seconds.

c) Incubation in anti-fibrinogen antiserum diluted 1:1000 for 1 hour at room temperature.

d) Incubation with peroxidase-conjugated anti-antibodies for 30 minutes.

e) Incubation in a solution of orthophenylenediamine (0.5 g/l) and 0.01% $H_2O_2$ in 0.1M citrate buffer, pH=4.5.

f) Addition of 2M $H_2SO_4$ and reading of absorbance at $\lambda$=450 nm.

Blood-compatibility test a) Venous blood (18 ml) was tapped from a healthy donor into 2.0 ml of a solution of hirudin in saline (500 IE/ml) (Hirudin is a thrombin inactivator).

b) The blood was filled into coated and non-coated tubes and allowed to incubate for 2 hours at room temperature.

c) 1 ml of blood was drawn into a syringe containing 0.2 ml diatube® and the mixture was centrifugated at 5000 g for 30 minutes at +3° C.

d) The supernatant was collected and the amount of β-thromboglobuline using a commercial kit (Diagnostica Stago).

Results

The results of the tests above are presented in table I and II. Table I shows that the amount of fibrinogen adsorbed to the tubes is reduced by the coating with ethyl-hydroxyethyl-cellulose. Table II shows that the amount of β-thromboglobuline released from the platelets during: incubation with blood is also reduced by the coating with ethyl-hydroxyethyl-cellulose.

TABLE I

| Amount of surface adsorbed fibrinogen as measured by the ELISA | | | | | | | |
|---|---|---|---|---|---|---|---|
| | teflon | polyurethane | polypropene | latex rubber | polyvinyl | silicone rubber | polystyrene |
| uncoated | 0.953 | 0.868 | 0.406 | 0.220 | 0.439 | 0.794 | 0.634 |
| EHEC (35° C.)* | 0.242 | 0.188 | 0.304 | 0.110 | 0.268 | 0.246 | 0.005 |
| EHEC (45° C.)* | 0.969 | 0.420 | 0.308 | 0.153 | 0.274 | 0.560 | 0.016 |
| Klucel ™ ** (<RT)* | 1.042 | 0.922 | 0.434 | 0.131 | 0.203 | 0.722 | |

Footnotes:
*flocculation temperature of the polymer in distilled water.
**propyl-hydroxypropylcellulose

TABLE II

| Amount of β-thromboglobuline released as measured by the ELISA | | |
|---|---|---|
| | teflon | polyurethane |
| uncoated | 1.38 | 1.67 |
| EHEC (35° C.) | 0.44 | 0.85 |

We claim:

1. Article exhibiting at least one hydrophobic surface of glass, metal or a hydrophobic polymer coated with a blood compatible surface layer, wherein the blood compatible surface layer consists of an adsorbed ethyl-hydroxyethyl-cellulose having a flocculation temperature of about 35°–40° C.

2. The article according to claim 1 wherein the hydrophobic polymer surface is polytetrafluoroethylene.

3. The article according to claim 1 or 2 which is a catheter, tube or a device for sampling or storage of blood.

4. The article according to claim 1 or 3 which is a heart-lung machine exhibiting at least one hydrophobic aluminium surface with a coating of a blood compatible surface layer.

5. Process for coating a blood compatible surface layer on a medical article having a hydrophobic substrate surface of glass, metal or polymer, comprising;
   (a) selecting an ethyl hydroxyethyl cellulose having a flocculation temperature of about 35°–40° C.; (b) purifying and isolating said cellulose by repeated heat flocculation and centrifiguration; (c) exposing said surface of glass, metal or polymer to a solution of said cellulose at a temperature below flocculation; and d) allowing said solution to adsorb to said surface.

6. The process according to claim 5 wherein the hydrophobic surface is polytetrafluoroethylene which is exposed to a solution of ethylhydroxyethylcellulose.

7. A method for the manufacture of a medical article having a blood compatible hydrophobic surface comprising the coating of a substrate material of glass, metal or hydrophobic polymer with a surface layer consisting of an adsorbed hydrophobized alkylated cellulose having a flocculation temperature of about 35°–40° C.

8. The method for the manufacture of a medical article having a blood compatible surface according to claim 7 wherein the substrate is polytetrafluoroethylene coated with a surface layer consisting of an adsorbed ethylhydroxyethylcellulose.

* * * * *

UNITED STATES PATENT AND TRADEMARK OFFICE
CERTIFICATE OF CORRECTION

PATENT NO. : 5,728,437
DATED : March 17, 1998
INVENTOR(S) : Nygren et al.

It is certified that error appears in the above-indentified patent and that said Letters Patent is hereby corrected as shown below:

Col. 6, line 17 (claim 5), insert --hydrophobic-- after "compatible".

Signed and Sealed this

Twenty-ninth Day of June, 1999

Attest:

Q. TODD DICKINSON

*Attesting Officer*         *Acting Commissioner of Patents and Trademarks*